(12) United States Patent
Salter et al.

(10) Patent No.: US 12,291,704 B2
(45) Date of Patent: May 6, 2025

(54) UNIVERSAL TEST DEVICE, ASSEMBLY, AND METHOD

(71) Applicant: Charm Sciences, Inc., Lawrence, MA (US)

(72) Inventors: Robert Salter, Reading, MA (US); Paul Graham, Dracut, MA (US); Jeffrey Verrette, Haverhill, MA (US); Richard T Skiffington, North Reading, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 17/191,911

(22) PCT Filed: Nov. 13, 2020

(86) PCT No.: PCT/US2020/060436
§ 371 (c)(1),
(2) Date: Mar. 4, 2021

(87) PCT Pub. No.: WO2021/097225
PCT Pub. Date: May 20, 2021

(65) Prior Publication Data
US 2022/0348861 A1 Nov. 3, 2022

Related U.S. Application Data

(60) Provisional application No. 62/935,270, filed on Nov. 14, 2019.

(51) Int. Cl.
C12M 1/34 (2006.01)

(52) U.S. Cl.
CPC .................... *C12M 41/36* (2013.01)

(58) Field of Classification Search
None
See application file for complete search history.

(56) References Cited

U.S. PATENT DOCUMENTS

| | | | | |
|---|---|---|---|---|
| 10,495,563 B1* | 12/2019 | Skiffington | ........ | G01N 15/1463 |
| 10,563,164 B1* | 2/2020 | Skiffington | ............ | C12M 23/04 |
| 11,009,446 B1* | 5/2021 | Skiffington | ............ | C12M 41/36 |
| 2004/0101951 A1 | 5/2004 | Vent et al. | | |
| 2005/0051723 A1* | 3/2005 | Neagle | ................... | C12M 41/48 |
| | | | | 250/306 |

(Continued)

FOREIGN PATENT DOCUMENTS

WO WO2017189948 11/2017

OTHER PUBLICATIONS

International Search Report and Written Opinion for PCT Application No. PCT/US2020/060436 dated Feb. 3, 2021.

*Primary Examiner* — Nancy Bitar
(74) *Attorney, Agent, or Firm* — MacCord Mason PLLC

(57) ABSTRACT

Reader and plate methods, operations, and systems for observing a biological sample are shown and described. In one embodiment, a device for observing biological growth, when present, on a growth plate, includes an imaging device and a variable positioning nest. The nest may include a first sunken frame to receive a first growth plate, and an offset second sunken frame to receive a distinct second growth plate in an operating position offset about the first operating position.

15 Claims, 10 Drawing Sheets

(56) References Cited

U.S. PATENT DOCUMENTS

| | | | | |
|---|---|---|---|---|
| 2006/0281143 | A1* | 12/2006 | Liu | C12M 23/34 |
| | | | | 435/297.2 |
| 2018/0371394 | A1* | 12/2018 | Ho | C12M 29/24 |
| 2020/0080044 | A1* | 3/2020 | Markovsky | C12Q 1/06 |

* cited by examiner

UNIVERSAL TEST DEVICE, ASSEMBLY, AND METHOD

This application claims the benefit of PCT application US2020/60436, filed Nov. 13, 2020, which claims priority to U.S. provisional application No. 62/935270, filed Nov. 14, 2019, all of which are incorporated herein by reference in their entireties.

FIELD OF THE TECHNOLOGY

The present disclosure relates generally to biological testing, and more particularly to improved methods and operation of test plates and readers.

BACKGROUND

It is desirable to provide rapid, effective detection and identification of various and numerous microorganisms in test samples, such as samples of water, food, such as milk, and body fluids. Microorganisms of interest include all aerobic bacteria and specific bacterial groups, such as coliforms. Other microorganisms of interest include a variety of yeast, molds, and the like.

Classical methods for culturing various microorganisms for detection and identification thereof include the spread plate method, the pour plate method and the liquid medium method. In these traditional methods and devices, biological testing is used to identify and quantify the presence of biological matter in samples. Often, these results are used to diagnose biological concerns and begin remedial measures. Particularly in the food industry, where testing is very cost-sensitive, early and accurate diagnosis is desired. In addition, reducing human error is desired, particularly where users might not be laboratory-trained technicians. Tests used must, therefore, be user-friendly and inexpensive without sacrificing accuracy. Further, conventional systems and methods fail to provide proper and efficient plate loading, alignment, and activation.

Therefore, Applicants desire systems and methods without the drawbacks presented by the traditional arrangements.

SUMMARY

In accordance with the present disclosure, devices and methods of operating improved plate readers are provided to observe, enumerate and/or monitor biological test development. This disclosure provides improved devices and methods that are convenient, efficient, and safe for the user, particularly when used to align and activate readers supporting differing growth plates to quantify biological development, when present.

In one embodiment, a device for observing biological growth, when present, on a growth plate includes an imaging device and an alignment nest comprising a first sunken frame adapted to receive a first growth plate in a first operating position, and an offset second sunken frame adapted to receive a distinct second growth plate in an operating position offset about the first operating position.

In certain examples, the second frame is aligned substantially perpendicular about the first frame. The first frame may be positioned substantially coplanar with the second frame. The device may include a first size plate about a Y-axis orientation with respect to the imaging device, and adapted to align a second size plate about an X-axis orientation with respect to the imaging device.

In particular examples, the first frame includes a first elongated foot aperture and a first opposing small foot aperture, and the second frame includes a second elongated foot aperture and a second opposing small foot aperture. The second frame may include a finger extension protruding about the second elongated foot aperture. The first frame and second frame may share an overlapping portion.

In certain examples, the first frame may align a first size growth plate, and the second frame adapted to align a growth plate distinct in size than the first size growth plate. The first frame may align a first size growth plate, and the second frame adapted to align a growth plate smaller in size than the first size growth plate. The first size growth plate may include about a five milliliter well. The second size growth plate may include about a one milliliter well. The device may include a user interface adapted for selecting a plate type selection chosen between at least two plate type selections.

In particular examples, the device may include a nest having a proximate extension aperture adapted to receive an inverted growth plate's proximate extension. The device may include a nest having a distal platform aperture adapted to receive an inverted growth plate's distal platform. The device may include an image processing engine adapted to perform a colony counting to monitor the biological growth, when present.

In one embodiment, an assembly for monitoring biological growth, when present, includes a first frame portion in optical alignment with an imaging device and associated with a first image resolution; and a second frame portion aligned substantially perpendicular about the first frame portion and in optical alignment with the imaging device and associated with a second image resolution.

In particular examples, the assembly includes a variable positioning tray holder nest comprising a pair of offset proximate extension apertures and a pair of offset distal platform apertures. The assembly may include an image processing engine adapted to perform colony counting to monitor the biological growth, when present. The assembly may include a user interface in electrical communication with the imaging device for selecting a plate type selection. The assembly may include a first size growth plate having a recessed well with a sunken wall protruding below an upper face, and including a second size growth plate distinct from the first size growth plate, and having a recessed well with a sunken wall protruding below an upper face.

In certain embodiments, a device for observing biological growth, when present, on a growth plate, includes an imaging device and a nest to align a first size plate about a Y-axis orientation with respect to the imaging device, and to align a second size plate about an X-axis orientation with respect to the imaging device.

In certain examples, the first size growth plate includes about a five milliliter well. The nest may receive an inverted first size growth plate. The inverted growth plate may be aligned parallel or below a raised boundary of the nest to retain the growth plate in a semi-fixed position. The second size growth plate may have about a one milliliter well. The nest may receive an inverted second size growth plate. The inverted growth plate may be aligned parallel or below a raised boundary of the nest to retain the growth plate in a semi-fixed position.

In particular examples, a user interface may select a plate type selection chosen between at least two plate type selections. The plate type selection may include a five milliliter well growth plate selection and about a one milliliter well growth plate selection.

In one embodiment, an assembly for monitoring biological growth, when present, includes a first frame in optical alignment with an imaging device having a first resolution; and a second frame aligned substantially perpendicular about the first frame and in optical alignment with the imaging device having a second resolution.

In certain examples the first resolution comprises about a ten megapixel resolution image, and the second resolution comprises about a five megapixel resolution image. The assembly may include a variable positioning tray holder nest comprising a pair of offset proximate extension apertures and a pair of offset distal platform apertures. The nest may receive a distinct size growth plate and transport the growth plate into a focal alignment with the imaging device.

In particular examples an image processing engine performs colony counting to monitor the biological growth, when present. The user interface may be in electrical communication with the imaging device for selecting a plate type selection. The assembly may include a first size growth plate having a recessed well with a sunken wall protruding below an upper face. The assembly may include a second size growth plate distinct from the first size growth plate, and having a recessed well with a sunken wall protruding below an upper face. In certain examples, the assembly includes an illumination system. Further, in particular examples the second resolution may produce a cropped border image.

In certain embodiments a device for observing biological growth, when present, on a growth plate, includes an imaging device and an alignment nest comprising a first sunken frame adapted to receive a first growth plate in a first operating position, and an offset second sunken frame adapted to receive a distinct second growth plate in an operating position offset about the first operating position.

In particular examples the second frame is aligned substantially perpendicular about the first frame. The first frame may include a first elongated foot aperture and a first opposing small foot aperture. The first frame may include a pair of first opposing small foot apertures. The second frame may include a second elongated foot aperture and a second opposing small foot aperture. The second frame may include a pair of second opposing small foot apertures.

In certain examples, the second frame includes a finger extension protruding about the second elongated foot aperture. The first frame and second frame may share a common optical center point. The first frame may align a first size growth plate, and the second frame may align a growth plate distinct in size than the first size growth plate. The first frame may align a first size growth plate, and the second frame may align a growth plate smaller in size than the first size growth plate. The first size growth plate may be about a five milliliter well. The second size growth plate may include about a one milliliter well.

In particular examples, a user interface may select a plate type selection chosen between at least two plate type selections. The plate type selection may be chosen from a first size growth plate selection and a second size growth plate selection. The nest may receive an inverted first size growth plate. The nest may receive an inverted second size growth plate. The inverted growth plate may be aligned parallel or below a raised boundary of the nest to retain the growth plate in a semi-fixed position.

In certain examples, the nest includes a proximate extension aperture to receive an inverted growth plate's proximate extension. The nest may have a distal platform aperture to receive an inverted growth plate's distal platform. In some examples, the device may include an illumination system and/or a housing.

In particular embodiments, in a device for enumerating biological growth, when present, a frame adapted to receive at least one growth plate may include a first size plate within a first frame alignment; and a second size plate within a second frame aligned substantially ninety degrees from the first frame alignment. In certain examples an optical center point of the first frame is aligned with an optical center point of the second frame. In certain examples, the first frame is aligned substantially coplanar with the second frame.

In certain examples, the first size plate includes a distal elongated platform adapted to align into a first elongated foot aperture. The first size plate may have at least one proximate extension adapted to align into a first opposing small foot aperture. The first size growth plate may include about a five milliliter well. The second size plate may include a distal elongated platform adapted to align into a second elongated foot aperture.

The second size plate may include at least one proximate extension adapted to align into a second opposing small foot aperture. The second size growth plate may include about a one milliliter well.

In one embodiment, in a device for enumerating biological growth, when present, on a growth plate, a method includes selecting a plate type between a first size plate selection and a second size plate selection; and loading a growth plate in a variable positioning nest consisting essentially of positioning the first size plate in a first alignment and positioning a second size plate in a second alignment.

In one example, loading the growth plate in the nest includes aligning an inverted growth plate in a sunken support frame. The method may include aligning either the first size inverted growth plate parallel or below a raised boundary in a semi-fixed position, or aligning the second size inverted growth plate parallel or below a raised boundary in a semi-fixed position. The method may include positioning an inverted growth plate's recessed well about a focal alignment with an imaging device. The method may include positioning an inverted growth plate's proximate extensions within a nest's corresponding proximate extension aperture. The method may include positioning an inverted growth plate's distal platform within a nest's corresponding distal platform aperture. The method may include transporting the growth plate from a loading position into a focal alignment with an imaging device.

In one embodiment, a device for monitoring biological growth, when present, on a growth plate, includes an illumination system, an imaging device positionable about the illumination system, a housing and a tray holder nest comprising a sunken frame to receive the growth plate, and wherein the tray holder nest receives the growth plate and transports the growth plate into a focal alignment with the imaging device.

In another embodiment, an assembly for monitoring biological growth, when present, includes a reader having a plate imaging unit with an imaging device and a tray holder nest comprising a proximate extension aperture and a distal platform aperture, and wherein the tray holder nest receives the growth plate and transports the growth plate into a focal alignment with the imaging device; a processor in electrical communication with the reader and having an image processing engine adapted to perform colony counting to monitor the biological growth, when present; a user interface in electrical communication with the imaging device for selecting a plate type selection chosen between at least two plate type selections; and at least one growth plate having a recessed well with a sunken wall protruding below an upper face.

In yet another embodiment, in a device for monitoring biological growth, when present, on a growth plate, a method comprises selecting a plate type between at least two plate type options on a user interface; loading the growth plate in a tray holder extending from the device; and transporting the growth plate into a focal alignment with an imaging device.

In certain examples, selecting a plate type includes indicating a plate type selection on a graphical user interface. For illustrative purposes only, the plate selection may include E coli and coliform plate selection, an aerobic bacteria plate selection, a yeast and mold plate selection, a heterotrophic plate selection, a combination thereof, and the like.

In particular examples, loading the growth plate in the tray holder includes aligning an inverted growth plate in a sunken support frame. For instance, the inverted growth plate may be aligned parallel or below a raised boundary to retain the growth plate in a semi-fixed position, i.e. any of the arrangements shown and described herein. For example, the method may include positioning an inverted growth plate's recessed well within a tray holder's recessed well aperture. Further, the method may include positioning an inverted growth plate's proximate extensions within a tray holder's proximate extension aperture. In certain examples, a pair of proximate extensions may align within the tray holder's pair of opposing proximate extension apertures.

In certain examples, loading the growth plate in the tray holder includes positioning an inverted growth plate's distal platform within a tray holder's distal platform aperture. For instance, transporting the growth plate into the device may include manually traversing the growth plate into focal alignment with the imaging device. Transporting the growth plate may include traversing the growth plate along a single radial axis. Transporting the growth plate may include traversing the growth plate into contact with a mechanical backstop. In addition, certain examples include loading average and background images, imaging the growth plate, and comparing the background image and growth plate image for yielding a background-subtracted count.

In another embodiment, in a device for monitoring biological growth, when present, on a growth plate, a method of aligning the growth plate for monitoring comprises depositing the growth plate in a tray holder external of the device; and transporting the growth plate into to a focal alignment with an imaging device.

In some examples, depositing the growth plate in the tray holder includes manually aligning an inverted growth plate in a sunken support frame. The operation may include aligning the inverted growth plate parallel or below a raised boundary adapted to retain the growth plate in a semi-fixed position. Further, the operation may include positioning an inverted growth plate's recessed well within the tray holder's recessed well aperture. The operation may include positioning an inverted growth plate's proximate extension within the tray holder's proximate extension aperture. In certain examples, a pair of proximate extensions may be positioned within the tray holder's pair of opposing proximate extension apertures. Further, the operation may include positioning an inverted growth plate's distal platform within the tray holder's distal platform aperture.

In certain examples, transporting the growth plate includes traversing the growth plate from a position adjacent the imaging device to a second processing position within the device. Transporting the growth plate may include traversing the growth plate along a single radial axis into the device. In some examples, transporting the growth plate includes traversing the growth plate in contact with a mechanical backstop, for instance thereby defining an alignment cradle aligning the growth plate in a processing position or the like.

Yet another embodiment includes selecting a plate type between at least two plate type options on a user interface. Selecting the plate type may occur prior to activating a plate imaging.

In certain examples, a plate type selection may include an *E-coli* and coliform plate selection, an aerobic bacteria plate selection, a yeast and mold plate selection, a heterotrophic plate selection, sub-categories, including plate types associated with particular test groups and end products, a combination thereof, and the like. In certain operations, selecting the *E-coli* and coliform plate selection initiates a monitoring sequence detecting and enumerating coliform bacteria on the growth plate. The operation may include loading average and background associated with the *E-coli* and coliform plate selection, for instance stored in the processor, user interface, or similar device or cloud storage. Further, the operation may include cropping an average image to yield active plate portions, cropping background images, and dividing the average image by the background image to yield a background-subtracted image. In yet other examples, selecting aerobic bacteria plate selection initiates a monitoring sequence of detecting and enumerating aerobic bacteria on the growth plate. The method may include cropping an average image to yield active plate portions, cropping background images, and dividing the average image by the background image to yield a background-subtracted image.

In further embodiments, an assembly for monitoring biological growth comprises a reader having a plate imaging unit with an imaging device and a tray holder, and wherein the tray holder receives the growth plate externally from the plate imaging unit and transports the growth plate into the plate imaging unit to a focal alignment with the imaging device; a processor in electrical communication with the reader and having an image processing engine adapted to perform colony counting to monitor the biological growth, when present; a user interface in electrical communication with the reader and to display a result display; and at least one growth plate having a recessed well with a sunken wall protruding below an upper face.

In some examples, the assembly includes an illumination system having an upper illumination dome having a plurality of light emitting diodes and a lower backlight diffuser. The reader, processor, and user interface may be integral with one another. However, in other examples the reader, processor, and/or user interface may be aligned substantially adjacent to one another on a bench top or other site-specific alignment. The reader may have a base plate including a backstop and an opposing open portion. The tray holder may include a sunken support frame adapted to receive and retain an inverted plate in a semi-fixed position. The tray holder may include a stationary end rotatably affixed to the base plate, and a traversing end adapted to allow entry and exit into the base plate along a single radial axis. Further, the growth plate may include a pair of opposing proximate extensions adjacent the recessed well and extending above the upper face, and a distal raised platform adjacent the recessed well and extending above the upper face.

In another embodiment, a device for monitoring biological growth, when present, on a growth plate comprises a reader having a housing with a plurality of openings, a plate imaging unit with an illumination system, an imaging device positionable about the illumination system, and a tray holder, and wherein the tray holder receives a growth plate externally through at least one opening and transports the growth plate into the plate imaging unit to a focal alignment with the imaging device; and a processor in electrical communication with the imaging device and having an image processing engine adapted to perform colony counting to monitor the biological growth, when present.

In particular examples, the housing has a top imaging aperture. Typically, the imaging device is aligned with the top imaging aperture. Further, the imaging device may be spaced offset from the top imaging aperture.

In some examples, an alignment bracket is positioning the illumination system about the imaging unit. For instance, the alignment bracket may include a lower fitting affixed to the illumination system and an upper fitting affixed to the imaging unit. The lower fitting and upper fitting may be positioned together with at least one adjustment. In certain examples, the at least one adjustment includes an off-axis adjustment.

In certain examples, a user interface is in electrical communication with the processor. Further, the tray holder may receive and retain a growth plate having a recessed well with a sunken wall protruding below an upper face, a pair of opposing proximate extensions adjacent the recessed well and extending above the upper face, and a distal raised platform adjacent the recessed well and extending above the upper face. The tray holder may include a stationary end rotatably affixed to the baseplate. The tray holder may include a sunken support frame adapted to receive and retain the plate in a semi-fixed position. The tray holder may have distal platform aperture, a well aperture, and pair of opposing proximate apertures are adapted to receive and mate with a corresponding inverted growth plate's recessed well, pair of opposing proximate extensions, and the distal raised platform. In addition, the device may include a baseplate includes at least one mechanical backstop defining an alignment cradle to align the tray holder in a processing position.

Yet another embodiment of the disclosure is a reader having a housing with a plurality of openings; a reader secured within the housing and having a plate imaging unit with an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device; a processor in electrical communication with the imaging device and having an image processing engine adapted to perform colony counting to monitor the biological growth, when present; a user interface in electrical communication with the reader and adapted to display a biological growth result display; and an alignment bracket having a lower fitting affixed to the illumination system and an upper fitting affixed to the imaging unit.

In some examples, the housing has a top imaging aperture. The imaging device may be aligned with the top imaging aperture. A fastener may semi-fix the lower fitting about the upper fitting. The lower fitting and upper fitting may be positioned together with at least one adjustment. The at least one adjustment includes an off-axis adjustment.

In particular examples, the tray holder receives and retains a growth plate having a recessed well with a sunken wall protruding below an upper face, a pair of opposing proximate extensions adjacent the recessed well and extending above the upper face, and a distal raised platform adjacent the recessed well and extending above the upper face. The tray holder may include a stationary end rotatably affixed to the baseplate. The tray holder may include a sunken support frame adapted to receive and retain the plate in a semi-fixed position. The tray holder may have a distal platform aperture, a well aperture, and pair of opposing proximate apertures are adapted to receive and mate with a corresponding inverted growth plate's recessed well, pair of opposing proximate extensions, and the distal raised platform.

In certain examples, a baseplate includes at least one mechanical backstop defining an alignment cradle to align the tray holder in a processing position. The illumination system may include an upper illumination dome having a plurality of light emitting diodes. Further, the illumination system may include a lower backlight diffuser.

In some examples, the reader, processor, and user interface are aligned substantially adjacent to one another on a bench top. Further, the reader, processor, and user interface may be integral with one another. The assembly may include at least one growth plate having a pair of opposing proximate extensions adjacent the recessed well and extending above the upper face, and a distal raised platform adjacent the recessed well and extending above the upper face.

Further embodiments include a method for monitoring biological growth, when present, on a growth plate comprises receiving at least one growth plate in a tray holder and transporting the growth plate into a focal alignment with an imaging device; selecting a plate type input chosen from at least a first plate type identifier and a second plate type identifier; imaging the growth plate with an imaging device positioned above the tray holder; and counting biological growth, when present, on the growth plate.

In particular examples, the first plate type identifier includes an aerobic count. The aerobic count may include lighting settings. In addition, the aerobic count may include imaging settings. The second plate type identifier may include an *E-coli* and coliform count, or the like. The *E-coli* and coliform count may include lighting settings. Further, the *E-coli* and coliform count includes imaging settings.

In certain examples, the method includes receiving the growth plate externally from a plate imaging unit. Further, the method may include transporting the growth plate along a single radial axis into a focal alignment with the imaging device. Counting biological growth may include marking bacterial colonies. In addition, marking may include circling bacterial colonies. For instance, the method may include displaying the circled bacterial colony counts on a user interface.

In some examples, selecting a plate type input includes manual selecting the plate type identifier on a user interface. Selecting a plate type input may include selecting a plate type identifier icon on a user interface. Further, selecting a plate type input may include voice commanding a selection of the plate type identifier.

In another embodiment, a reader for monitoring biological growth, when present, on a growth plate, comprises a plate imaging unit having an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device; a user interface having at least two plate type identifiers; and a processor having an image processing engine adapted to perform colony counting to monitor the biological growth, when present, on the growth plate.

In particular examples, the first plate type identifier includes an aerobic count. The aerobic count may include a corresponding lighting setting. The aerobic count may include a corresponding imaging setting. The second plate type identifier may include an *E-coli* and coliform count. The aerobic count may include a corresponding lighting setting. The aerobic count may include a corresponding imaging setting. The user interface may include a graphical display of the biological growth counting, when present, on the growth plate.

In some examples, the plate imaging unit may include a baseplate substantially parallel to the tray holder. The baseplate may include at least one mechanical backstop defining an alignment cradle to align the tray holder in a processing position. The baseplate may include a backlight indent adapted to receive a backlight. The tray holder may include a stationary end rotatably affixed to the baseplate. The tray holder's stationary end may include a bearing. The tray holder may include a sunken support frame adapted to receive and retain the plate in a semi-fixed position. The tray holder may include a recessed distal platform aperture, a recessed well aperture, and a pair of opposing proximate apertures. The growth plate may include a recessed well having a sunken wall protruding below an upper face, a pair of opposing proximate extensions adjacent the recessed well and extending above the upper face, and a distal raised platform adjacent the recessed well and extending above the upper face. The tray holder's distal platform aperture, well aperture, and pair of opposing proximate apertures may receive and mate with a corresponding inverted growth plate's recessed well, pair of opposing proximate extensions, and the distal raised platform.

In another embodiment, a plate imaging unit for imaging biological growth, when present, on a growth plate, the unit comprising: an illumination system, including an upper illumination dome having a plurality of light emitting diodes and a lower backlight diffuser; a base plate including a backstop and an opposing open portion; a tray holder including a sunken support frame adapted to receive and retain an inverted plate in a semi-fixed position, a stationary end rotatably affixed to the base plate, and a traversing end adapted to allow entry and exit into the base plate along a single radial axis; and a plurality of plate type identifiers.

In a further embodiment, a plate imaging unit for imaging biological growth, when present, on a growth plate includes a mounting foundation; a base plate; a backlight diffuser positioned between the mounting foundation and the base plate, a tray holder coplanar with base plate, and wherein the tray holder having a stationary end rotatably affixed to the base plate and a traversing end to allow entry and exit from the unit along a single radial axis; an illumination dome having a plurality of light emitting diodes positioned above the base plate; and a high resolution camera centered above the illumination dome.

In particular examples, the mounting foundation includes a plurality of couplers adapted to affix the base plate. The baseplate may include a backstop and an open front portion, thereby defining an alignment cradle to align the tray holder in a processing position. The baseplate may include an optics aperture. The baseplate may include a protruding mounting portion to rotatably retain the plate holder's stationary end.

In certain examples, the tray holder includes a body supporting a sunken support frame to retain the plates in a semi-fixed position. The tray holder may include an extension neck protruding from the body and supporting an alignment assembly. The extension neck may include a spring plunger catch and the alignment assembly includes a support block, a ball knob, and a plunger aligning the ball knob about the support block.

In some examples, the assembly includes an image processor that is operably connected to a high resolution camera. The processor may be housed in a laptop computer, tablet, or the like. The processor may have image inputs and pipeline parameter inputs. In some examples, the parameter inputs include calibration inputs and/or fixed inputs based on specific plates.

In another embodiment, a reader for monitoring biological growth, when present, on a growth plate, includes a plate imaging unit and a processor. The plate imaging unit may have an illumination system, an imaging device positionable above the illumination system, and a tray holder, and wherein the tray holder receives the growth plate externally from the plate imaging unit and transports the growth plate along a single radial axis into the plate imaging unit to a focal alignment with the imaging device. The processor may have an image processing engine to perform colony counting to monitor the biological growth, when present, on the growth plate.

In certain examples, the plate imaging unit includes a baseplate that is substantially parallel to the tray holder. The baseplate may include at least a first stop and an adjacent second stop defining an alignment cradle to align the tray holder in processing position. The baseplate may include a backlight indent adapted to receive a backlight. The tray holder may include a stationary end rotatably affixed to the baseplate. The tray holder's stationary end may include a bearing. The tray holder may include a sunken support frame adapted to receive and retain the plate in a semi-fixed position. The tray holder may include a recessed distal platform aperture, a recessed well aperture, and a pair of opposing proximate apertures.

In particular examples, the growth plate includes a recessed well having a sunken wall protruding below an upper face, a pair of opposing proximate extensions adjacent the recessed well and extending above the upper face, and a distal raised platform adjacent the recessed well and extending above the upper face. The tray holder's distal platform aperture, well aperture, and pair of opposing proximate apertures may receive and mate with a corresponding inverted growth plate's recessed well, pair of opposing proximate extensions, and the distal raised platform.

In a further embodiment, a plate imaging unit for imaging biological growth, when present, on a growth plate, may include an illumination system, including an upper illumination dome having a plurality of light emitting diodes and a lower backlight diffuser; a base plate including a backstop and an opposing open portion; and a tray holder including a sunken support frame adapted to receive and retain an inverted plate in a semi-fixed position, a stationary end rotatably affixed to the base plate, and a traversing end adapted to allow entry and exit into the base plate along a single radial axis.

In yet a further embodiment of the present disclosure a reader for semi-continuously monitoring biological growth on a growth plate includes an illumination system illuminating a top and side of the growth plate; an imaging device positionable above the illumination system; and a drawer assembly spaced below the illumination system and to transport the growth plate along a single axis into the reader to a focal alignment with the imaging device and eject the growth plate from the reader. Typically, the imaging device semi-continuously monitors an isolated area of interest on the growth plate.

In some examples, the illumination system is a light box including a perimeter lighting frame having a first, second, third and fourth light sides, the first and second sides opposing one another and the third and fourth sides opposing one another and the first and second sides being substantially perpendicular to the third and fourth sides. Further, the perimeter lighting frame may include a plurality of light emitting diodes. The perimeter lighting frame may include a diffuser to soften light emitted from the light emitting diodes on the growth plate. The perimeter lighting frame may focus light on a top and at least one side of the growth plate.

In particular examples, the drawer assembly includes a slide support face. The drawer assembly may include a raised boundary on opposing sides of the slide support face. The drawer assembly may include opposing walls adjacent the boundary. The drawer assembly may include a traversing tongue to secure the growth plate.

The reader may include a mounting arm supporting the imaging device. The imaging device may be a video image capture device. The video image capture device may be a USB camera. The imaging device may image the growth plate in multiple quadrants. The imaging device may image the growth plate as a whole. Further, the image processor may be operably connected to the imaging device.

Another embodiment of the present disclosure is an optical bench having an upper housing having a light box; and a lower housing having a drawer assembly externally receiving and transporting the growth plate, for instance into the reader to a focal alignment with the imaging device and eject the growth plate from the reader. Typically, the light box substantially encloses the growth plate and the drawer assembly aligns the growth plate in substantially fixed focal length distance within the imaging device's field of vision.

In some examples, the imaging device performs a semi-continuous imaging of an isolated area of interest on the growth plate. The growth plate may include a reference grid, wherein the imaging device uses the reference grid to navigate and provide a plurality of pixel map images of the fixed area for monitoring bacterial colony development. For instance, the imaging device may generate a pixel map on the growth plate, whereby the pixel map is an indication of the biological development when present. The growth plate may include a plurality of quadrants having a plurality of pixel map values. The pixel map value may be a prediction of a final test result prior to the test result being visible to the human eye. Further, the pixel map value may be an observation of early stage biological development.

In particular examples, the light box includes a light perimeter frame. The light perimeter frame may include a plurality of light emitting diodes. The light perimeter frame may include a diffuser to soften light emitted from the light emitting diodes on the growth plate. Further, the light perimeter frame may focus light on a top and at least one side of the growth plate.

In some examples, the drawer assembly is moveable along an axis to allow entry and exit from the reader. The drawer assembly may include a slide support face. The drawer assembly may include a raised boundary on opposing sides of the slide support face. The drawer assembly may include opposing walls adjacent the boundary. The drawer assembly may include a traversing tongue adapted to secure the growth plate. The optical bench may include a mounting arm supporting the imaging device. The imaging device may be a video image capture device, for instance a USB camera.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
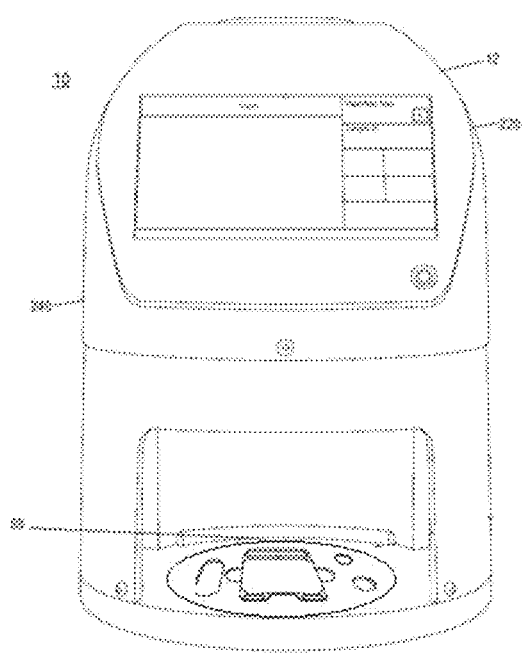
FIG. 1 is a front perspective view of one embodiment of a growth plate aligned in first operating position according to the present disclosure.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 2:
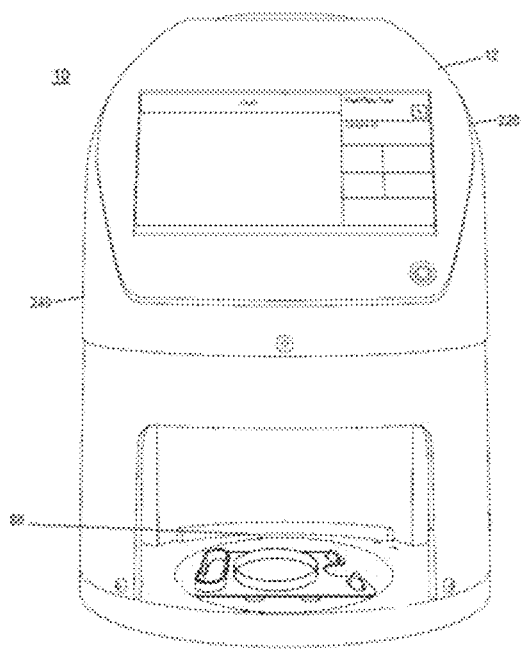
FIG. 2 is a front perspective view of one example of a growth plate aligned in a second operating position according to the present disclosure.

Referring now to the drawings in general, and FIGS. 1 and 2 in particular, it will be understood that the illustrations are for the purpose of describing embodiments of the disclosure and are not intended to limit the disclosure or any invention thereto. As seen in the various figures, reader systems and assemblies are shown embodied according to the present disclosure for biological growth counting with proper plate seating and activation, increased sample throughput, direct data results reporting, and processed plate image storage. The reader system 10 generally images biological development, when present, on an individual growth plate 20, 20' and/or a plurality of growth plates, or similar testing medium. The assembly generally includes receiving elements, activation elements, plate imaging elements to monitor biological development, and processing elements to monitor, quantify, or the like biological growth, when present.

FIGS. 1-3 and 7-7a illustrate embodiments of plate imaging unit to generally receive, image, and remove any of the peel plates shown and described herein. The readers, devices, and assemblies herein may include a variety of outer supports or housing to secure and protect internal components. For instance, as shown in FIG. 1, an outer housing 240 may protect internal components. The housing 240 may include a plurality of openings to allow access to the tray holder nest 66 and like elements shown and described herein. In certain examples, the plate imaging unit may include a mounting foundation, a backlight diffuser, a base plate, a tray holder nest 66, an illumination dome 84, and an optics imaging device 12. Although as illustrated and described herein, the imaging unit, the illumination unit, and the nest unit may include a variety of elements and arrangements. In certain embodiments, the tray holder nest includes a traversing end, including a swivel or rotating end, that transports plates about the reader, for instance along a single radial axis along track 88. Further, the illumination dome 84 may include an optics enclosure to generally enclose the imaging device. The illumination dome may evenly illuminate corresponding optical alignment about the plate and prevent reflections on the plate surface.

As introduced in FIGS. 1 and 2, the reader may include a tray holder nest 66 having a sunken support frame to receive and retain distinct growth plates in a semi-fixed operating position for any of the procedures and processes shown and described herein. As shown in FIG. 1 the nest may align a first size growth plate in a first operating position, and as shown in FIG. 2 align a second size growth plate in a second operating position that is generally offset from the first operating position. The second operating position may be substantially co-planar and perpendicular to the first operating position. And in certain examples, the nest 66 may align a first size plate about a Y-axis orientation and align a second size plate about an X-axis orientation. Those of ordinary skill in the art having the benefit of this disclosure will recognize a variety of plate sizes, including but not limited to differing size surface areas, well volumes, depths, lengths, widths, geometry, and the like. In certain examples (for instance as introduced in FIGS. 8-9 and 8a and 9a) a first size growth plate 20 may have a first size well 15, including but not limited to about a five milliliter well, whereas a second size growth plate 20' may have a second size well 15', including but not limited to about a one milliliter well. Other examples of at least two distinct growth plate embodiments as shown and described herein include additional volumes and dimensions.

Figure 4:
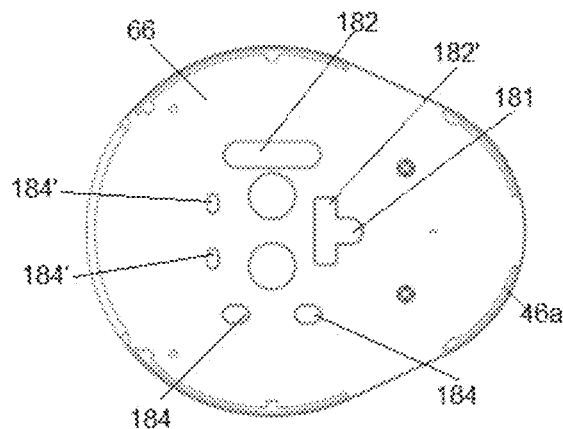
FIG. 4 is a top view of isolated elements of a nest.
Figure 4A:
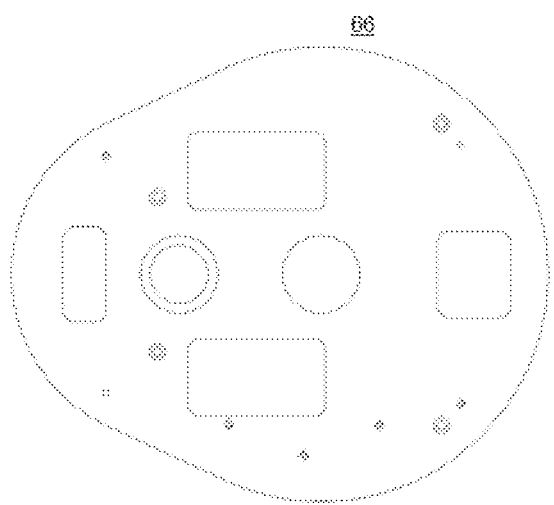
FIG. 4a is a bottom view of isolated elements of the nest introduced in FIG. 4.

FIGS. 4 and 4a illustrate a particular embodiment of nest 66 having a first sunken frame to receive a first growth plate in a first operating position, and an offset second sunken frame to receive a distinct second growth plate in an operating position offset, for instance about co-planar and/or perpendicular, to the first operating position. The nest 66 may be surrounded, in part, by a raised boundary 46a, thereby providing a plurality of differing cavity alignments to receive and retain the plates.

In particular examples, the first frame includes a first elongated foot aperture 182 and at least one, including two or more, first opposing small foot aperture 184 to mate with a corresponding, including but not limited to a five milliliter well, inverted growth plate's recessed well, pair of opposing proximate extensions, and distal raised platform as shown and described herein. As shown in FIG. 4, the second frame may be aligned substantially overlapping in part and perpendicular about the first frame. The second frame may be scaled to size distinct from the first frame to support multiple differing size plates. The second frame may include a first elongated foot aperture 182' and at least one, including two or more, second opposing small foot aperture 184' to mate with a corresponding, including but not limited to a one milliliter well, inverted growth plate's recessed well, pair of opposing proximate extensions, and distal raised platform as shown and described herein. The second frame may have an extension 181, for instance a finger extension or the like, protruding from the second elongated foot aperture 182' to assist removing, or otherwise manipulating, a smaller size growth plate, or the like, in the second frame.

In certain examples, the tray holder nest may have a body, a traversing end, and an opposing stationary end. The stationary end may be rotatably affixed, or the like, to a base plate, while the traversing end moves about a single axis to allow entry and exit from the plate imaging unit.

Figure 3:
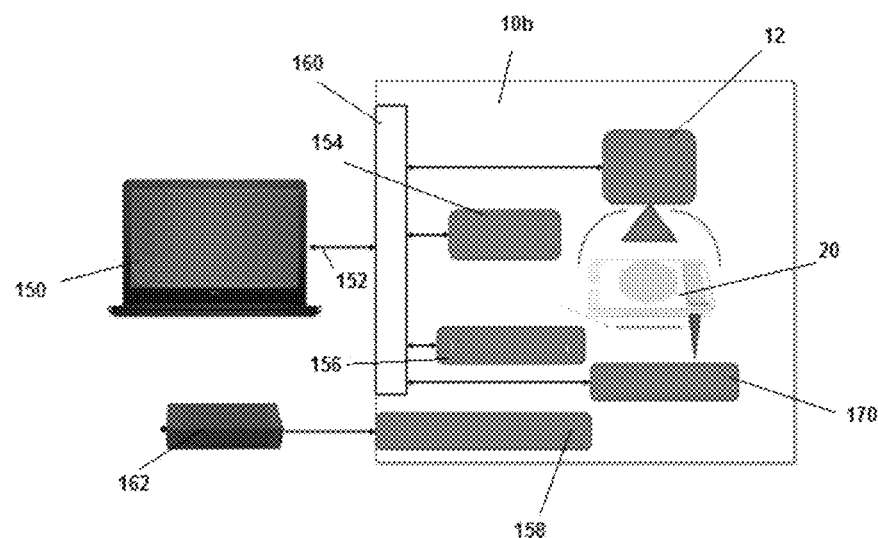
FIG. 3 is a schematic view of plate reader elements according to one embodiment of the disclosure.

Typical reader assembly embodiments include plate imaging elements and user interface elements, either in electrical communication with one another or combined into an integral assembly as shown in FIG. 1, although those of ordinary skill in the art having the benefit of this disclosure will recognize additional arrangements and embodiments incorporating the elements shown and described herein. FIG. 3 illustrates one overview of useful reader assembly elements, including a plate imaging unit, reader system, a user interface, computer processor. The assembly typically includes an image processing engine to perform any of the colony counting, monitoring, observing, enumerating of biological growth, when present, on the growth plate as illustrated and described herein. In particular examples, the computer processor is a qualified laptop, tablet, or the like running plate analyzer processing unit. Alternative examples include remote processing and the like.

In particular embodiments, the reader system may include an imaging device 12 adjacent to the plate 20 in an imaging position. An alignment bracket may secure the elements in a semi-fixed position. For instance, a lower fitting may be affixed to the illumination system, housing, or the like. Similarly, an upper fitting may be affixed to the imaging unit, devices, housing, or the like. The lower fitting and upper fitting may be secured about one another in a variety of configurations and alignments, including, but not limited to, with a fastener or similar linkage. The lower fitting and upper fitting may be positioned together with at least one adjustment. In certain examples, the adjustment includes an off-axis, i.e. a horizontal, vertical, or the similar, adjustment.

The system may include sensors to indicate any of the alignment and/or alert system errors shown and described herein. Further, the system may include illumination control to control any of the illumination elements and aspects shown and described herein. In addition, the system may include power distribution to control and distribute power for any of the elements and aspects shown and described herein, and a power supply, including but not limited to an external power supply. In particular examples, the system includes an OCR system identification and/or code reader to assign sample identification information, and in some examples count results described herein. Certain reader system elements are in electrical communication with a user interface, for instance a computer processor, via a unified communication interface and/or USB connection 152, or the like. Those skilled in the art having the benefit of this disclosure will recognize additional electrical communication platforms, including adjacent, integral, and/or remote connection arrangements.

Figure 1A:
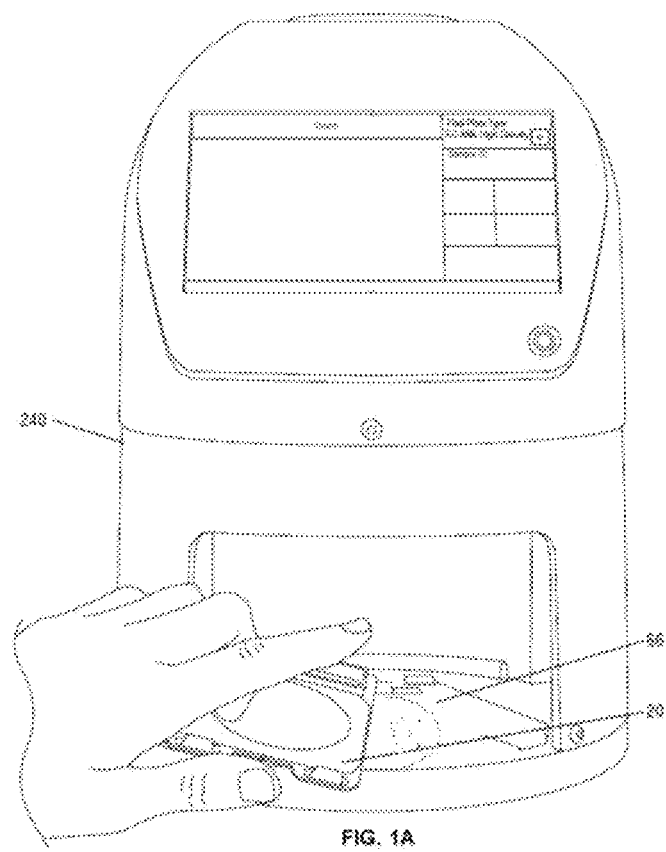
FIG. 1A is a front perspective view of one example of loading a growth plate into the plate reader introduced in FIG. 1.
Figure 11:
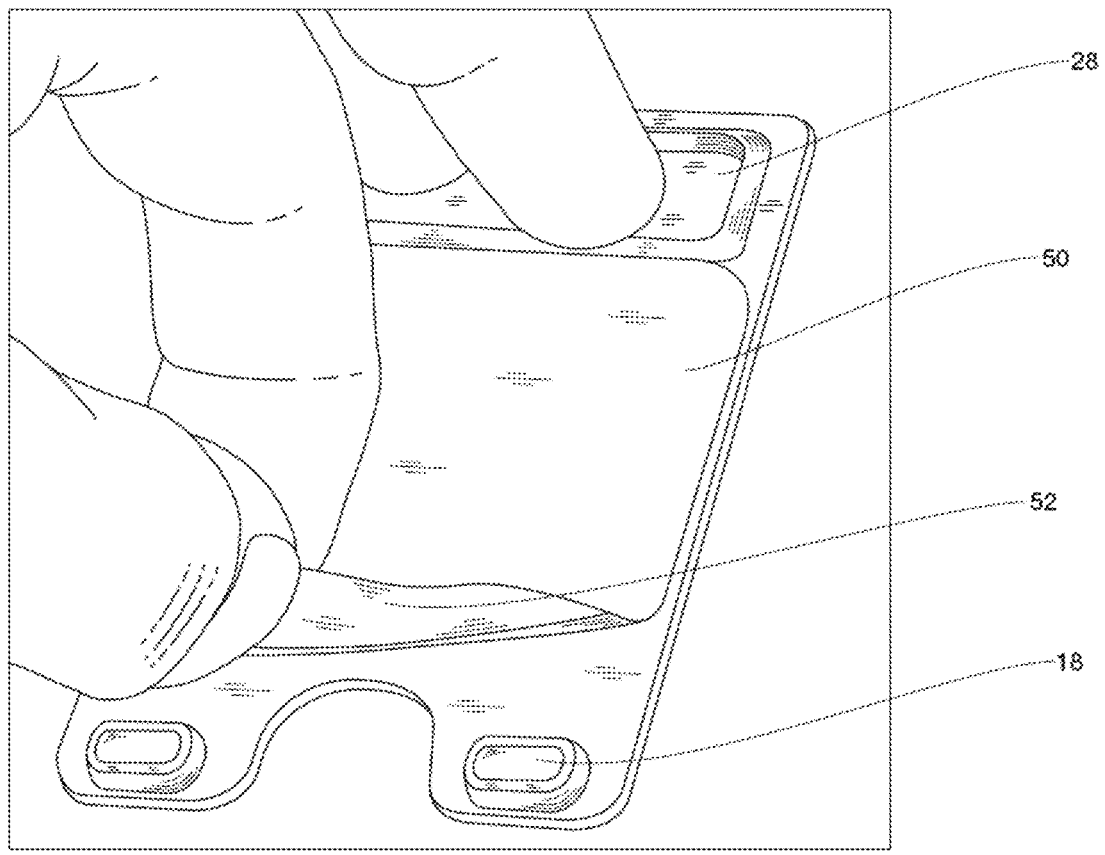
FIG. 11 is a top perspective view of one embodiment of a peel plate according to the disclosure.

Operation of the assembly may be triggered in a variety of ways, including, but not limited to, manual selection on a user interface, voice activation, remote or timed start, manual positioning of the plate, and the like. FIGS. 1a and 11 show examples of a manual positioning of the plate. As illustrated, a user may manually load the plate into tray holder 66 (including aligning any of the growth plate features with any of the nest features shown and described herein) which may, in certain examples, extend from the device, i.e. outside and adjacent imaging aspects of the device. The user may then transport the tray holder into the device, for instance manually transport, along a fixed axis 88 into a focal alignment with an imaging device in the reader system. In certain examples, the tray holder snaps into place with a position bearing to confirm a centered position with the imaging device within the reader system.

Figure 5A:
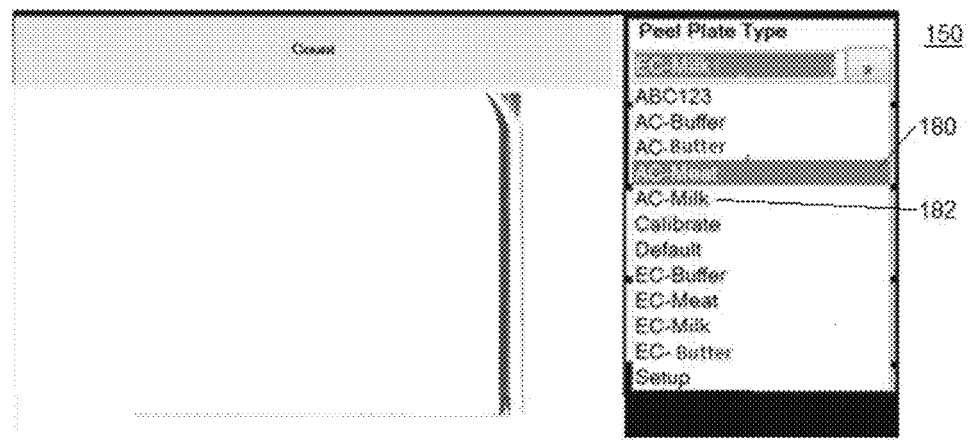
FIGS. 5A-5B are views of a user interface embodiment in a plate selection mode according to the disclosure.
Figure 5B:
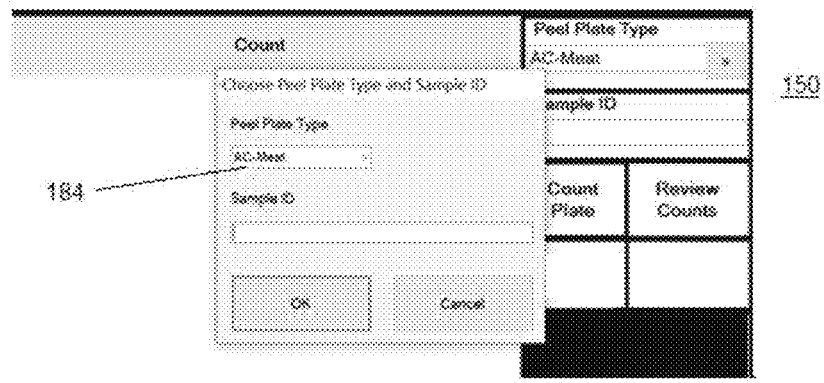
Figure 5C:
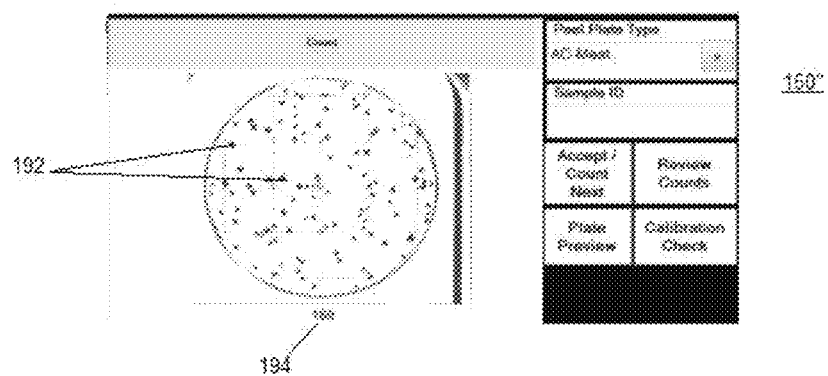
FIG. 5C is a view of a user interface embodiment in a results display mode according to the disclosure.
Figure 5D:
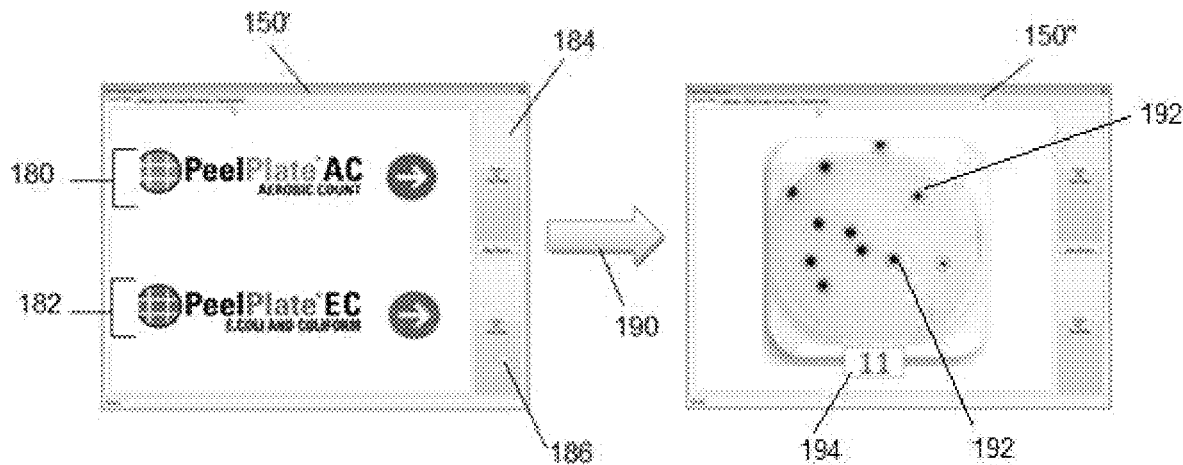
FIG. 5D is a view of a user interface embodiment in a plate selection mode and results display mode according to the disclosure.
Figure 6:
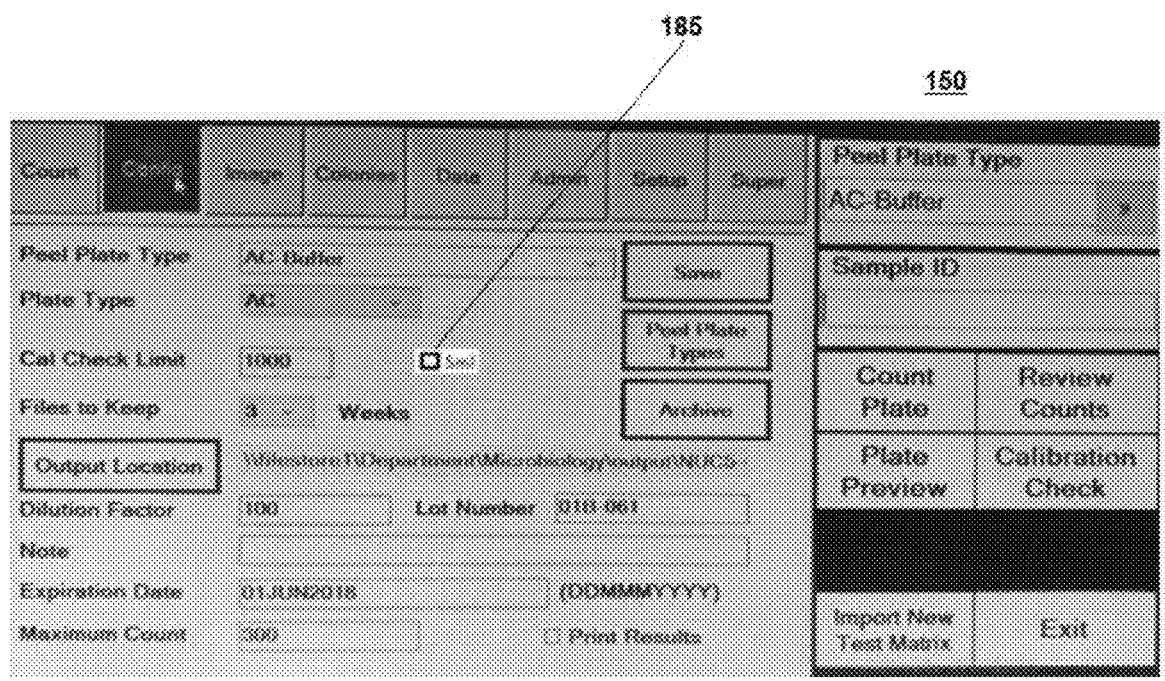
FIG. 6 is a view of a user interface embodiment with a plate size selection according to the disclosure.
Figure 7:
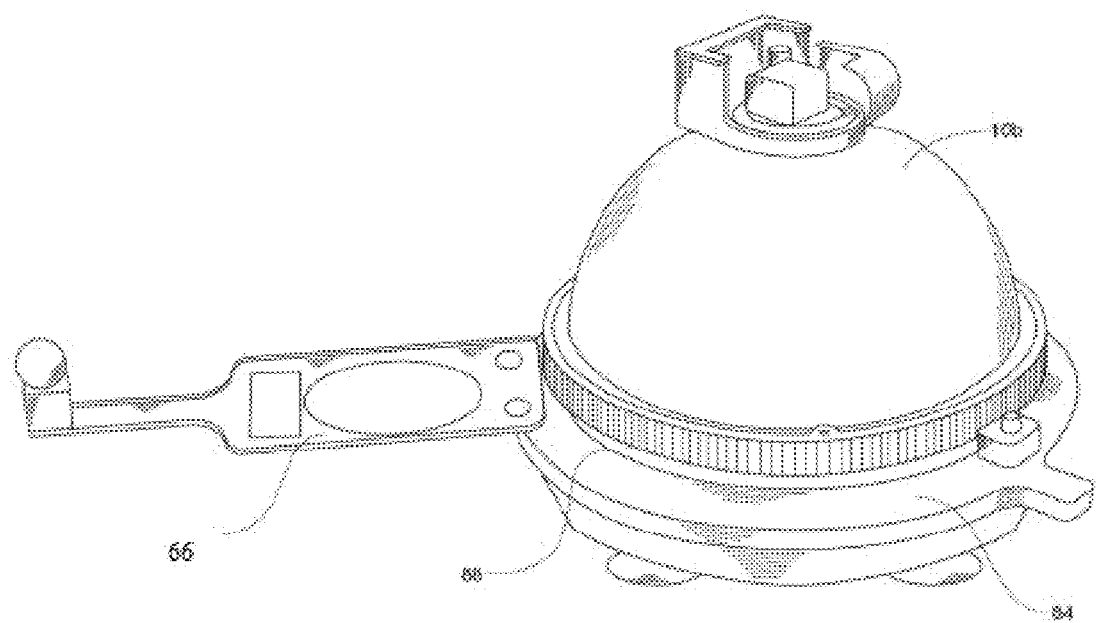
FIG. 7 is a front perspective view of a plate reader system.
Figure 7A:
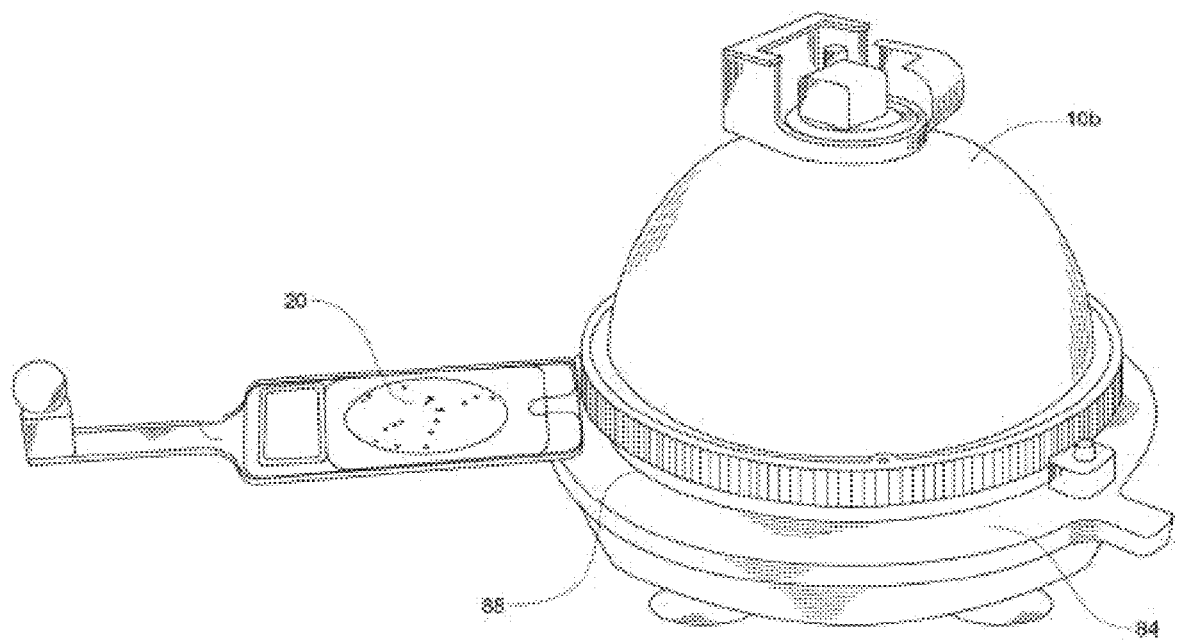
FIG. 7a is a front perspective view of the embodiment in FIG. 7, loaded with one example of a growth plate.

In use, the operator manually selects the proper plate type and/or count operation to be performed by the assembly. As shown in FIG. 5A-6, examples of the user interface selection screen 150 includes a plate type identifier. For instance, the selection screen 150 may include a plurality of plate type selection identifiers 180, 182, including a plurality of identifiers and/or sub-category plate type identifiers. The operator may manually select the plate type selection, for instance via clicking, touching, speaking, or the like, the proper icon, voice activating the assembly to types of plates to count, or similar selection processes. As shown, the user interface 150, 150' may include a first plate count input selection 184, and in some examples an additional, or plurality, of input selections. Further as shown in FIG. 6, the interface selection screen 150 may include a plate size identifier 185. In particular embodiments the plate size identifier 185 may allow a selection between at least a first size plate selection and a second size plate selection. In certain examples, the first size plate selection may include a five milliliter well 15 plate 20 as illustrated in FIGS. 8a and 9a, whereas a second size plate selection may include a one milliliter well 15' plate 20'. Those of ordinary skill in the art having the benefit of this disclosure will recognize additional plate sizing, dimensions, scaling, and the like are within the spirit of the disclosure. Other examples of the selection screen includes a plurality of other manual plate type count input selections and/or manual plate type count input sub-category selections.

In particular examples, a selection of a plate size identifier 185 triggers a resolution change for any of the imaging shown and described herein. For illustrative purposes only: a first plate size identifier selection associates a first resolution with any of the imaging examples and embodiments, whereas a second plate size identifier selection associates a second resolution, including an altered, transformed, flipped, modified, cropped, adjusted, varied, reformed or the like with any of the imaging examples and embodiments. For instance, a user may select, toggle, or otherwise indicate imagery matrix prompt for a specified growth plate, and in particular examples, a specified plate well, including but not limited to between a five milliliter well and a one millimeter well, or the like.

For illustrative purposes only, a first plate type identifier may include an aerobic count used for the detection and enumeration of aerobic bacteria in dairy and food decimal dilutions. The aerobic count may include lighting settings, imaging settings, and similar counting settings as recognized by those skilled in the art having the benefit of this disclosure. A second plate type identifier may include an *E-coli* and coliform count used for detection and enumeration of coliform bacteria, including *E-coli* in dairy, food, and water. The *E-coli* and coliform count may include lighting settings, imaging settings, and similar counting settings. Another plate type identifier may include a yeast and mold count for detection and enumeration of yeasts and/or molds in foods and environment. In addition, another plate type identifier may include a heterotrophic plate count used for detection and enumeration of water samples.

In certain examples, a user selects a plate type (including any of the plate type selections shown and described herein). The user may load a blank plate for quality control assurance and/or calibration as described herein. The device may then capture an image of the blank plate. In certain examples, the image is stored on a storage device, processor, cloud storage, hard drive, or the similar means. The user manually loads the plate with the sample and selects the count plate indicator to initiate a particular sequence, for instance the plate is typically manually loaded and the indicator is selected prior to imaging the plate. The imaging device may capture one, or multiple frames averaged together for greater consistency, to create an image using pixel-to-pixel averages for noise reduction of frames.

For illustrative purposes only, when the second plate type identifier for an *E-coli* and coliform count is selected, the system loads average and background images. The system may then crop an average image to yield an image of active portions of the pate as recognized by those skilled in the art having the benefit of this disclosure. The system may then crop background image, divide the average image by the background image to yield background-subtracted image. The system may then invert the image and threshold the image in any of the methods shown and described herein, to identify primary objects, including colonies. The image may then be cropped again, and the color objects may be unmixed. For instance in the *E-coli* and coliform count, the system separates (unmixes and the like) and counts the red color counts and the blue color counts. In particular examples, the results are recorded and saved to a database by any of the procedures described herein.

Similarly, when a first plate type identifier for an aerobic count used for the detection and enumeration of aerobic bacteria is selected, the system loads average and background images. The system may then crop an average image to yield an image of active portions of the pate as recognized by those skilled in the art having the benefit of this disclosure. The system may then crop background image, divide the average image by the background image to yield background-subtracted image. The system may then mask colors of the imagery, typically the mask may be defined in the graphical user interface. The color objects may be unmixed. The system then thresholds the image in any of the methods shown and described herein to identify primary objects, including colonies. In particular examples, the results are recorded and saved to a database by any of the procedures described herein. Those skilled in the art will recognize additional operations and methods, including any image counting method 190, triggered by a selected plate type selection with the benefit of this disclosure.

In particular examples, the user interface display 150" presents a count result 194. The user interface display 150" result may include marking bacterial colonies in a variety of graphical and/or narrative displays. For instance, the display 150" may present circled bacterial colony counts 192 on an image of the plate, or the like. The processed image 150"

may include a coded name, for instance marked on a barcode or the like as described herein, and a CSV file with corresponding colony count information. The output image and an output report will vary depending on the type of plate being processed. For example, an aerobic count may indicate a unified count of all colonies, whereas an *E-coli* count contain color categorized colonies.

In certain examples, mounting foundation may include one or a plurality of supports, including suction cups, fittings, braces, and the like, to support any of the plate imaging units shown and described herein about a flat surface or similar laboratory bench. Fasteners, as well as a grommet and spring plunger may secure the base plate about the mounting foundation and/or other bodies. Further, a backlight diffuser, for instance the backlight box may be positioned between the base plate and mounting foundation to generally diffuse flat lighting under the plate to enhance silhouette detection.

In certain examples, the assemble includes a mounting foundation of the image station for supporting the plate imaging unit. The mounting foundation may include one or more mounting holes to mate with the base plate. Further, the mounting foundation may include a foundation framing, or similar solid supporting, to support the load of any of the elements and examples shown and described herein. In certain examples, the mounting foundation may include base plate couplers and backlight diffuser couplers so support and provide clearance for foundation and lighting elements. Those of ordinary skill in the art having the benefit of this disclosure will recognize additional framing and support elements and alternatives.

In particular examples, a baseplate may generally align and receive any of the tray holder nests shown and described herein. The baseplate may include an open portion having a substantially flat entry/exit and an opposing backstop. One example of a stop includes a horizontal portion intersecting two vertical portions, thereby defining a rigid stop for an alignment cradle. In certain examples, an optics aperture is aligned in the alignment cradle. In addition, the baseplate may include a protruding mounting portion to rotatably retain a plate holder's stationary end.

In certain examples, an extension neck may extend from the tray holder body to support an operating assembly. The operating assembly may include a support block, a plunger, and a ball knob. Further, the extension neck may support a spring plunger catch. On the opposing side of the extension neck, a tapered portion supports the stationary end. The stationary end may have a bearing aperture to secure a bearing, for instance a needle roller bearing or the like, to provide any of the loading positions and the radial rotation shown and described herein.

Those of ordinary skill in the art having the benefit of this disclosure will recognize that any of the growth plates shown and described herein may include plate-like devices, Petri dish culture devices, and the like. Typically, the growth plate 20 includes a growth area where biological growth, or the like, may develop. As shown the growth area may be transparent and may have a recessed well that is useful for culturing various microorganisms.

Figure 8:
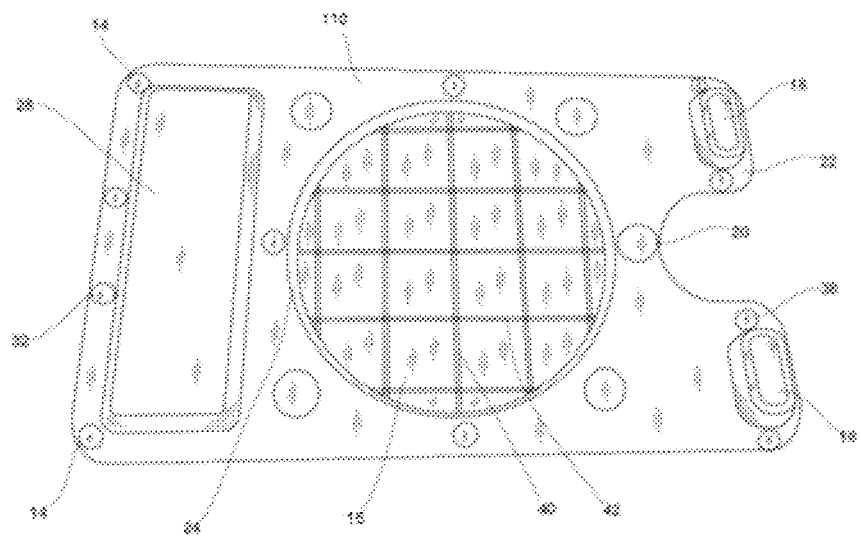
FIG. 8 is a top perspective view of one embodiment of a growth plate according to the disclosure.
Figure 9:
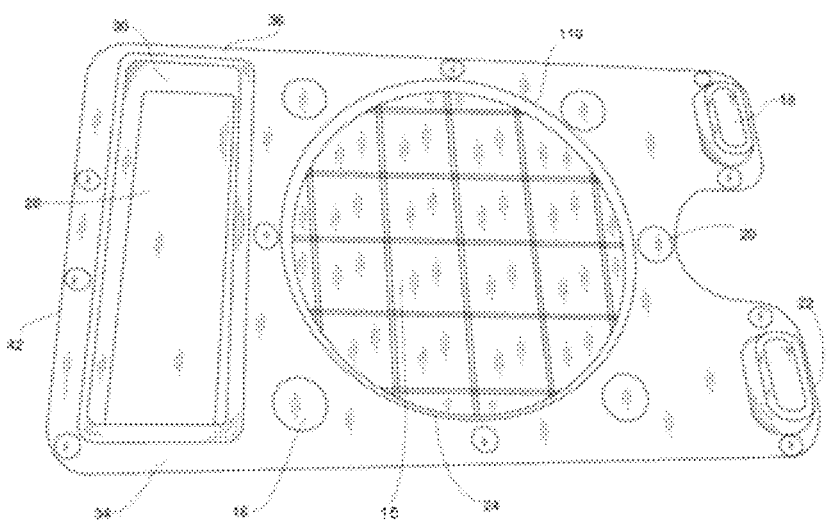
FIG. 9 is a bottom perspective view of the growth plate introduced in FIG. 8.
Figure 8A:
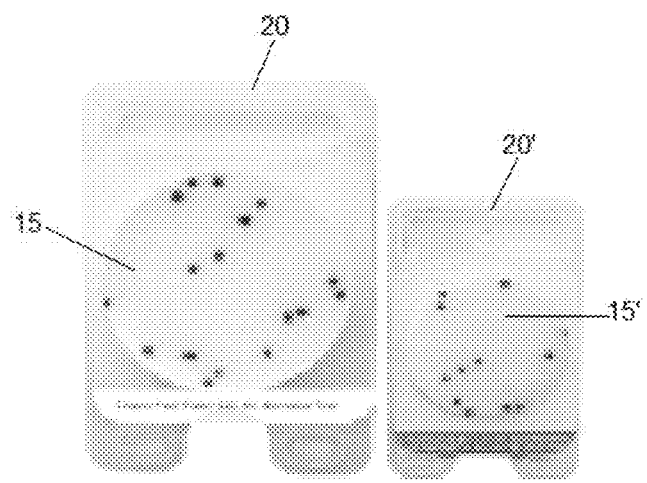
FIG. 8a is a top perspective view of one embodiment of multiple growth plates according to the disclosure.
Figure 9A:
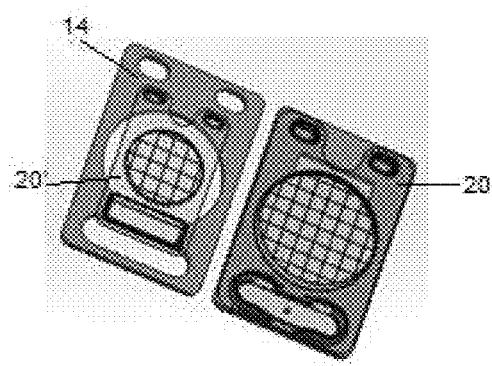
FIG. 9a is a top perspective view of one embodiment of multiple growth plates according to the disclosure.
Figure 10:
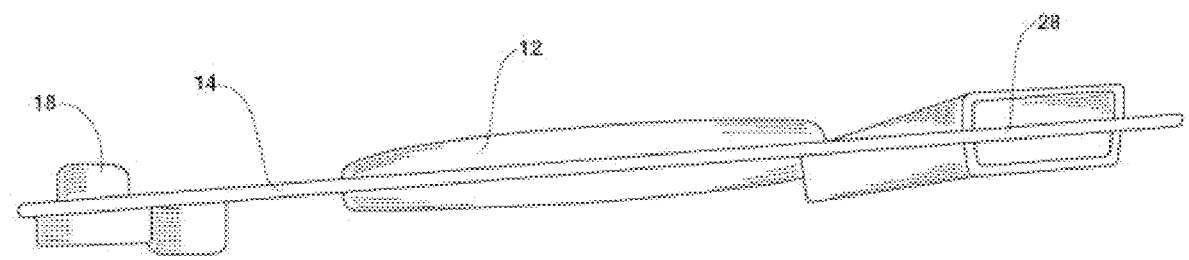
FIG. 10 is a side perspective view of a growth plate.

FIGS. 8-9a introduce examples of a culture device growth plate for enumerating and/or detecting a microorganism from a sample that is useful for the reader examples and embodiments shown and described herein. The peel plate 110 typically is a semi-rigid waterproof plate onto which sample may be applied to enumerate microorganisms and the like. As seen in FIG. 8, one example of the peel plate 110 includes a recessed well 12, a distal raised platform 28, and opposing proximate tabs 22 having proximate extensions 28 to support stacked plates as shown and described herein. The upper face 14 of the plate typically has a top periphery 32 around the raised platform. The recessed well 12 includes a sunken wall 24 below the upper face 14. As shown in FIG. 8, the recessed well may include a grid, for instance having vertical line 40 and intersecting horizontal line 42 components useful for colony counting. In particular examples, the grid is molded, printed, and the like on the rear surface. The grid may be printed in a variety of ways, including inkjet printing, pad printing and the like. Regardless of the grid type, the grid is typically visible through the generally transparent culture device to the front surface and/or rear surface. The plate 110 is also typically transparent material so as to enable observation from the outside, including any of the printed grids shown and described herein.

FIG. 8 further shows the proximate end of the peel plate 110 includes an access indent 20 with opposing proximate tabs 22 between rounded corners 38. Typically, the proximate tabs 22 offset the proximate extensions, and the like, from the body of the plate, i.e. the well and the majority of the upper surface. Thereby the proximate tabs include proximate extensions 18 for alignment, stability, and support during testing/usage, including, but not limited to, layering and stacking plates in any of the arrangements and orientations shown and described.

FIGS. 9 and 11 show a bottom and side view, respectively, of one example of a peel plate 110 having a raised edge 30 extending above the lower face 16 to define the raised platform 28. Typically, the peel plate has a distal thickness 42 to support any of the elements and testing procedures shown and described herein.

FIG. 8 introduces one example of a peel plate 110 having a covered surface as shown and described herein. For instance, the peel plate 110 may be placed on a substantially level surface. The peel tab 52 may be lifted concurrently while pressure is applied to the raised platform 28 with the user's fingers, or the like. In particular examples, the tab 52 may be lifted vertically upwards and away to expose any of the culture media shown and incorporated herein. In particular the culture media is any dried media culture disc.

The processors described herein are typically in electrical communication, including USB connection, wireless, or the like, with the plate imaging unit. The processor may include an image processing engine to perform colony counting operations and the like. In particular examples, the image processing engine has image inputs and pipeline parameter inputs. Particular parameter inputs are determined by calibration, including any of the calibration steps and examples herein. Other fixed plate type parameters may be fixed. The image processing engine may generate a variety of outputs, for instance colony counting information.

An alternative embodiment of the illumination system 84 may include a beam splitter to minimize, or eliminate, reflections from appearing on the plate surface. Examples of the beam splitter include at least one mirrored surface, a glass prism, or similar optical device splitting a beam of light produced from any of the illumination system elements shown and described herein. In particular examples, the beam splitter is oriented directly above the plate surface, or the like, and the plurality of LEDs are aligned laterally and facing toward beam splitter on the same horizontal axis. In operation, the plurality of LEDs direct light toward beam splitter, and beam splitter directs the light to the plate surface. The beam splitter, plurality of LEDs, and imaging device, are positioned such that minimal, or no, reflections appear on the plate surface to produce any of the improved imaging and analysis shown and described herein. The beam splitter typically directs light from the plurality of LEDs perpendicularly to the plate surface. And in certain examples, the imaging device is aligned directly above beam splitter to mask the reflection of camera from the plate surface.

In alternative embodiments, the plate imaging unit may include an optics bench. In this example, the optics bench includes an upper housing and a lower housing. The upper housing may include an illumination system, for instance the light box, and an adjustment assembly. The lower housing may include a drawer opening having a slide support frame being repositionable about alignment assembly. The slide frame may secure a support tongue, a raised boundary on opposing sides of the support tongue, and adjacent opposing walls. The support tongue generally secures the peel plate in a semi-fixed position during alignment and operation.

Further, in alternative embodiments an imaging device may be aligned above the illumination system substantially surrounding the growth plate. The optics may be any of the imaging devices shown and described herein, including a camera to capture any of the still and video images supported by optics communication.

In some examples, the camera includes a moveable lens to manipulate the focal distance of the imaging device to capture a variety of pixel mappings. For instance, the camera lens may be moved closer to the plate or more distant from the plate to gather a variety of pixel mappings, depending on the particular testing sequence.

In some examples, the illumination system includes a plurality of light emitting diodes (LEDs), for instance ninety six, or the like, white LEDs. The light box may include a perimeter lighting frame having a first, second, third and fourth light sides to provide focused light on the top and sides of the peel plate. Further, the light box may include a diffuser.

In yet another alternative example, an imaging device is positioned on the mounting arm about the upper face of the housing. Those of ordinary skill in the art having the benefit of this disclosure will recognize the imaging device may include any optics electronics processing board. Further, the reader may include a processor to provide any of the imaging and analysis shown and described herein.

The vision system for any of the imaging devices shown and descried herein may utilize a grid, reference lines, markings, quadrants, and the like for consistent mapping of specified locations on and among the plates. Further, any of the imaging devices may gather pixel mapping data or values from the entire growth plate or any of the subsections shown and described herein.

In yet other embodiments, several imaging devices may be positioned throughout the reader for generating any of the images show and described herein at a variety of angles with respect to the growth plates. For instance, in some examples the reader may include at least a top and a bottom imaging device, while in other examples the reader may include one mobile imaging device that is capable of moving around, or within, the reader to capture images/scans from the top and bottom perspectives of the growth plates.

In use, the plate imaging unit may be a dynamic tool for monitoring biological agents and development on growth plates, or similar mediums. Generally, the reader system includes imaging technology for observing and quantifying biological growth, when present. In this way, Applicants have unexpectedly discovered the systems shown and described herein enhance the ability to observe changes in the plate development earlier than provided for in conventional systems. Further, the systems and methods herein predict a final result before the final result is actually visible by the human eye. For instance, the systems and methods herein are more sensitive than the human eye and conventional assemblies. In addition, the systems and methods herein monitor the growth plate to find variability prior to test development. For instance, the systems and methods herein establish a more accurate baseline for measuring changes in the growth plate than provided for in the conventional assemblies.

In use, the preliminary image may be first captured with any of the imaging devices shown and described herein under an install calibration. In one example, the settings that configure any optical system for ideal image capture may be predefined during the calibration phase of system installation. Periodic recalibration may be required due to system aging and metrological conditions. Calibration is achieved with pre-printed sample plates. For instance, optimization of lighting intensity, camera focus and camera exposure time may be defined at calibration time.

In one example, mechanical alignment of the growth plate 20 is achieved by drawing a digital circle around the sample area. This digital circle may be manipulated via keyboard, keystrokes to align the circumference and diameter with the sample plate area of interest. Typically, lighting intensity, exposure time, camera focus and mechanical alignment are configuration settings that remain constant after installation as shown and described herein.

As shown and described herein, the image area may be reduced to include only the area of interest that is predefined by the install calibration. Applicants have unexpectantly discovered this reduces processing time, in particular by not having to parse through uninteresting elements as understood by those skilled in the art having the benefit of this disclosure.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

What is claimed is:

1. A device for observing biological growth, when present, on a growth plate, said device comprising:
an imaging device and a substantially stationary alignment nest comprising a first sunken frame having a first orientation with a first size to receive an inverted first size growth plate in a first operating position, and an offset second sunken frame having a second orientation distinct from said first orientation and a second size distinct from said first size to receive an inverted distinct second size growth plate in an operating position being substantially perpendicularly offset about said first operating position and wherein said alignment nest having an upper surface maintaining said first sunken frame and said offset second sunken frame in a coplanar position about one another.

2. The device of claim 1, wherein said first frame positioned substantially coplanar with said second frame.

3. The device of claim 1, including a first size plate about a Y-axis orientation with respect to said imaging device, and adapted to align a second size plate about an X-axis orientation with respect to said imaging device.

4. The device of claim 1, wherein said first frame includes a first elongated foot aperture and a first opposing small foot aperture, and said second frame includes a second elongated foot aperture and a second opposing small foot aperture.

5. The device of claim 1, wherein said second frame includes a finger extension protruding about said second elongated foot aperture.

6. The device of claim 1, wherein said first frame and second frame share an overlapping portion.

7. The device of claim 1, wherein said first frame adapted to align a first size growth plate, and said second frame adapted to align a growth plate distinct in size than said first size growth plate.

8. The device of claim 1, wherein said first frame adapted to align a first size growth plate, and said second frame adapted to align a growth plate smaller in size than said first size growth plate.

9. The device of claim 8, wherein said first size growth plate includes about a five milliliter well.

10. The device of claim 8, wherein said second size growth plate includes about a one milliliter well.

11. The device of claim 7, including a user interface adapted for selecting a plate type selection chosen between at least two plate type selections.

12. The device of claim 1, including a nest having a proximate extension aperture adapted to receive an inverted growth plate's proximate extension.

13. The device of claim 1, including a nest having a distal platform aperture adapted to receive an inverted growth plate's distal platform.

14. The device of claim 1, including an image processing engine adapted to perform a colony counting to monitor said biological growth, when present.

15. A method of observing biological growth, when present, on a growth plate, said method comprising: aligning an inverted first size growth plate about a first sunken frame having an orientation to receive an inverted said first size growth plate in a first operating position and aligning an inverted second size growth plate distinct from said first size growth plate about an offset second sunken frame having an orientation to receive an inverted distinct second size growth plate in an operating position being substantially perpendicularly offset about said first operating position; and imaging said growth plate for observing said biological growth, when present, on said growth plate and wherein said alignment nest having an upper surface maintaining said first sunken frame and said offset second sunken frame in a coplanar position about one another.

* * * * *